United States Patent [19]

Knosp

[11] 4,218,244

[45] Aug. 19, 1980

[54] GOLD ALLOY FOR FIRING ON PORCELAIN FOR DENTAL PURPOSES

[75] Inventor: Helmut Knosp, Pforzheim, Fed. Rep. of Germany

[73] Assignee: Deutsche Gold- und Silber-Scheideanstalt vormals Roessler, Frankfurt, Fed. Rep. of Germany

[21] Appl. No.: 956,985

[22] Filed: Nov. 1, 1978

[30] Foreign Application Priority Data

Nov. 18, 1977 [DE] Fed. Rep. of Germany ....... 2751547

[51] Int. Cl.² .............................................. C22C 5/02
[52] U.S. Cl. ...................................... 75/165; 433/207
[58] Field of Search ................................ 75/165; 32/8

[56] References Cited

U.S. PATENT DOCUMENTS

| | | | |
|---|---|---|---|
| 3,413,723 | 12/1968 | Wagner et al. | 75/165 |
| 3,666,540 | 5/1972 | Burnett | 75/165 |
| 3,716,356 | 2/1973 | Burnett | 75/165 |
| 4,062,676 | 12/1977 | Knosp | 75/165 |

FOREIGN PATENT DOCUMENTS

| | | | |
|---|---|---|---|
| 2424575 | 12/1975 | Fed. Rep. of Germany | 75/165 |
| 957493 | 5/1964 | United Kingdom | 75/165 |

*Primary Examiner*—L. Dewayne Rutledge
*Assistant Examiner*—Peter K. Skiff
*Attorney, Agent, or Firm*—Cushman, Darby & Cushman

[57] ABSTRACT

Gold alloys for firing on porcelain for dental purposes are prepared from 80 to 90% gold, 5 to 15% platinum, 0.5 to 10% palladium, 0.5 to 3% rhodium, 0.1 to 3% indium, 0 to 3% tin and optionally 0.1 to 2% tantalum and/or tungsten in place of or in addition to the rhodium.

9 Claims, No Drawings

GOLD ALLOY FOR FIRING ON PORCELAIN FOR DENTAL PURPOSES

BACKGROUND OF THE INVENTION

The invention is directed to a yellow gold alloy for firing on porcelain for dental purposes according to German OS 24 24 575.8 and related Knosp U.S. Pat. No. 4,062,676 which contains beside gold, platinum, indium, tin and rhodium and/or tantalum and/or tungsten, but which also contains palladium. The entire disclosure of the Knosp U.S. patent is hereby incorporated by reference and relied upon.

In the dental prosthesis it is customary to cover crowns and bridges of special noble metal alloys with porcelain. Standing in the foreground is the idea of combining the good mechanical properties of the alloy and the aesthetic appearance and the tissue compatability of porcelain.

In the infancy of this art, it was tried to fire ceramic compositions or caps and structures of platinum-iridium alloys. Because of the poor workability of these high melting alloys and the incomplete harmonization of the properties with those of porcelain, however, there very frequently occur failures.

In the last years a series of special alloys have become known which, based on their physical and mechanical properties, substantially satisfy the requirements of the firing art. There are used alloys which contain 70 to 90% gold, 5 to 15% platinum, 0.5 to 10% palladium, 0.1 to 2% indium, 0.1 to 2% tin, as well as small additions of silver, copper, iron, iridium and rhenium.

All of the alloys, however, have the disadvantage that they exhibit a gray color. However, in dental alloys a yellow gold color is very much desired. Especially in visible, non-faced parts of a metal structure finished by a fired alloy a yellow color is desired for aesthetic reasons. Also, at those places of the structure on which the ceramic is molded somewhat thinly a living appearance is caused by a yellow color. Therefore, in recent years, there has not been a lack of attempts to produce alloys for firing which are considerably yellower in color than those previously known and which simultaneously conform in their physical and mechanical properties to the necessary industrial requirements.

There are known alloys which besides the above-mentioned constituents also contain nickel, titanium and zinc, as well as large amounts of copper. Besides, it was tried to attain a deepening of the yellow gold color by increasing the gold content and lowering the palladium content. However, all of these procedures can merely produce alloys which only come a little nearer the yellow gold color than the previous customary firing alloys. It has further been found that the properties of the alloys are unfavorably influenced through the named additives. For example, titanium causes a slag formation in melting and casting because of the high negative enthalpy of formation of its oxide; copper and, particularly zinc, very strongly lower the solidus temperature so that there can no longer be guaranteed a sufficient heat resistance of the alloy during the firing of porcelain. Furthermore, because of the ready volatility of zinc oxide, zinc has an unfavorable effect on the adhesion between alloy and porcelain.

It is known that palladium above all others very disadvantageously influences the color of gold alloys. Alloys containing over 70% of gold which contain palladium but no, or only a very little, copper and zinc appear gray or at most show a pale yellow color. In firing alloys palladium has the main task of increasing the solidus temperature and in combination with indium and/or tin makes possible a tempering since it is likewise known that in gold alloys containing additions of indium and/or tin the hardness depends very greatly on the palladium content. It was previously believed that the addition of palladium could not be eliminated.

In German OS 24 24 575.8 and Knosp U.S. Pat. No. 4,062,676, however, it has been proposed to use palladium free gold alloys for firing porcelain for dental purposes in order to obtain an intensive gold color. To obtain the most favorable mechanical properties, these alloys contain rhodium and/or tantalum and/or tungsten. The alloys according to German OS 24 24 575.8 contain 80 to 90% gold, 5 to 15% platinum, 0.1 to 2% indium, 0 to 2% tin, 0.05 to 0.5% iridium as well as 0.5 to 3% rhodium and/or 0.1 to 2% tantalum and/or 0.1 to 2% tungsten. The alloys according to Knosp U.S. Pat. No. 4,062,676 contain 60 to 90% gold, 5 to 35% platinum, 0.1 to 3% indium, 0 to 10% palladium, 0.5 to 3% rhodium, 0 to 3% tin, 0.1 to 2% tantalium and/or tungsten and 0.3 to 2% zinc.

Of course these alloys have a sufficiently high solidus temperature for the normal case, but for several use situations this is still too low.

Therefore, it was the problem of the present invention to find gold alloys for firing on porcelain for dental purposes which beside having an intensive gold color have higher solidus temperatures than the alloys according to German OS 24 24 575.8 and Knosp U.S. Pat. No. 4,062,676.

SUMMARY OF THE INVENTION

This problem was solved according to the invention by using alloys which besides 80 to 90% gold, 5 to 15% platinum and 0.5 to 3% rhodium contain 0.1 to 3% indium, 0 to 3% tin and 0.5 to 10% palladium. Besides or in place of rhodium, these alloys can also contain 0.1 to 2% tantalum and/or tungsten.

It has surprisingly turned out that the yellow coloring additions of rhodium and/or tantalum and/or tungsten are effective even in the presence of palladium which commonly produces a gray-white coloration in gold alloys. The use of palladium, in a given case at the expense of platinum, has the advantage that the solidus temperature of the alloys can be effectively increased. Thereby, the heat resistance in the porcelain firing is increased considerably so that a great bridge width can be refired with porcelain.

A partial replacement of the platinum by palladium furthermore, has the advantage that the hardness of the alloys are increased since it is particularly easy to attain a tempering by combinations of palladium and indium and/or tin. An increase of the indium and/or tin content to more than 2% in the presence of palladium in a surprising manner does not create an aggravated lowering of the solidus temperature, as actually was to be expected. Higher indium and/or tin contents than 2%, therefore, are practically exclusively for the benefit of a better tempering.

It has also been found surprisingly that the addition of iridium for grain refinement of the alloys of the invention can be eliminated. By the addition of rhodium and/or tantalum and/or tungsten, there is effected even without iridium a comparably equally good grain refinement in the structure.

Especially approved forms of the invention are alloys which contain 83 to 87% gold, 6 to 10% platinum, 3 to 6% palladium, 2 to 3% indium and 0.1 to 0.3% tantalum since these alloys have an excellent elongation at break and high elastic limit which are advantageous for dental uses. There has proven particularly advantageous in industrial use an alloy containing 84 to 85% gold, 8% platinum, 5% palladium, 2.5% indium and 0.1% tantalum.

The yellow color of the alloys of the invention surpasses even that of copper containing gold-platinum-cast alloys. Therefore, it is possible also to use the alloys of the invention as cast alloys for inlays, crowns and bridges or in combination with synthetic facings.

Unless otherwise indicated, all parts and percentages are by weight.

The alloys can consist essentially of or consist of the stated materials.

DESCRIPTION OF THE PREFERRED EMBODIMENTS

Several examples of compositions of the alloys of the invention are given in the following table:

TABLE

| Example Nr. | Composition in Weight % | | | | | | | | Melting Range in °C. | Vickershardness in HV | |
|---|---|---|---|---|---|---|---|---|---|---|---|
| | Au | In | Pd | Pt | Rh | Sn | Ta | W | | Soft | tempered |
| 1 | 87 | 1,5 | 3,4 | 7,0 | 0,5 | 0,5 | — | 0,1 | 1210 ... 1080 | 70 | 185 |
| 2 | 85 | 0,2 | 5,6 | 6,0 | — | 3,0 | — | 0,2 | 1200 ... 1090 | 95 | 200 |
| 3 | 85 | 2,5 | 4,4 | 8,0 | — | — | 0,1 | — | 1210 ... 1100 | 95 | 220 |
| 4 | 84 | 2,0 | 1,0 | 10,0 | 1,5 | 1,5 | — | — | 1220 ... 1090 | 105 | 220 |
| 5 | 81 | 1,5 | 6,0 | 6,9 | 2,6 | 1,0 | — | 1,0 | 1220 ... 1100 | 110 | 210 |
| 6 | 80 | 3,0 | 9,5 | 7,0 | — | — | 0,5 | — | 1230 ... 1120 | 115 | 220 |

What is claimed is:

1. A gold alloy having an intensive gold color and free from the gray-white coloration normally imparted to gold alloys containing palladium suitable for having porcelain fired thereon consisting of 80 to 90% gold, 5 to 15% platinum, 0.5 to 10% palladium, 0.1 to 3% indium, 0 to 3% tin and at least one member selected from the group consisting of 0.5 to 3% rhodium, 0.1 to 2% tantalum and 0.1 to 2% of tungsten.

2. A gold alloy according to claim 1 free from tin.

3. A gold alloy according to claim 1 free from rhodium.

4. A gold alloy according to claim 1 containing rhodium and tantalum and free from tungsten.

5. A gold alloy according to claim 1 containing rhodium and tungsten and free from tantalum.

6. A gold alloy according to claim 1 free from tin, rhodium and tungsten.

7. A gold alloy according to claim 1 consisting of 83 to 87% gold, 6 to 10% platinum, 3 to 6% palladium, 2 to 3% indium and 0.1 to 0.3% tantalum.

8. A gold alloy according to claim 7 consisting of about 84 to 85% gold, 8% platinum, 5% palladium, 2.5% indium and 0.1% tantalum.

9. A gold alloy according to claim 7 consisting of 85% gold, 2.5% indium, 4.4% palladium, 8.0% platinum and 0.1% tantalum.

* * * * *